(12) United States Patent
Rogers et al.

(10) Patent No.: US 8,442,284 B2
(45) Date of Patent: May 14, 2013

(54) SWEPT SOURCE OCT APPARATUS

(75) Inventors: John A. Rogers, Canterbury (GB); Mark Hathaway, Canterbury (GB)

(73) Assignee: Optos PLC (GB)

( * ) Notice: Subject to any disclaimer, the term of this patent is extended or adjusted under 35 U.S.C. 154(b) by 956 days.

(21) Appl. No.: 12/092,504

(22) PCT Filed: Oct. 31, 2006

(86) PCT No.: PCT/CA2006/001782
§ 371 (c)(1), (2), (4) Date: Oct. 7, 2008

(87) PCT Pub. No.: WO2007/051293
PCT Pub. Date: May 10, 2007

(65) Prior Publication Data
US 2009/0080739 A1  Mar. 26, 2009

(30) Foreign Application Priority Data
Nov. 2, 2005 (GB) .................................. 0522338.3

(51) Int. Cl.
*G06K 9/00* (2006.01)
(52) U.S. Cl.
USPC ......................................................... 382/128
(58) Field of Classification Search ........................ None
See application file for complete search history.

(56) References Cited

U.S. PATENT DOCUMENTS

| | | | |
|---|---|---|---|
| 7,075,658 B2 | 7/2006 | Izatt et al. | |
| 7,330,273 B2 * | 2/2008 | Podoleanu et al. | 356/497 |
| 7,391,520 B2 * | 6/2008 | Zhou et al. | 356/479 |
| 2001/0045513 A1 | 11/2001 | Kourogi et al. | |
| 2004/0076390 A1 * | 4/2004 | Dong Yang et al. | 385/116 |
| 2004/0254474 A1 * | 12/2004 | Seibel et al. | 600/473 |
| 2005/0018201 A1 * | 1/2005 | de Boer et al. | 356/479 |
| 2005/0036150 A1 | 2/2005 | Izatt et al. | |

FOREIGN PATENT DOCUMENTS

| | | |
|---|---|---|
| WO | WO 98/35203 A2 | 8/1998 |
| WO | WO 2004/002298 A1 | 1/2004 |
| WO | WO 2005/047813 A1 | 5/2005 |

OTHER PUBLICATIONS

Chih-Wei Lu, et al, "Multi-frequency-scan Optical Coherence Tomography for Resolution beyond the Fourier Transform Limit," Pacific Rim Conference on Lasers and Electro-Optics, 2005, Jul. 30-Aug. 2, 2005, pp. 191-192, CLEO/Pacific Rim 2005.
Jun Zhang, et al, "Swept Source Based Fourier Domain Functional Optical Coherence Tomography," 27th Annual International Conference of the Engineering in Medicine and Biology Society, 2005, Sep. 1-4, 2005, pp. 7230-7233, IEEE-EMBS 2005.

* cited by examiner

*Primary Examiner* — Jermele M Hollington
(74) *Attorney, Agent, or Firm* — Laubscher & Laubscher, P.C.

(57) ABSTRACT

A method of performing spectral OCT imaging on a target involves repeatedly scanning said target along a transverse scanning line with an object beam derived from an OCT interferometer having a narrowband source. The wavelength of the narrowband source is modulated over a range of wavelengths at a rate that is slow relative to the rate of scanning the target. The object beam returned from the target is detected to produce a set of data obtained from multiple scans along said scanning line over the entire range of wavelengths. The data is then processed to extract an OCT image (typically a B-scan) of the target containing depth information.

17 Claims, 2 Drawing Sheets

SWEPT SOURCE OCT APPARATUS

FIELD OF THE INVENTION

This invention relates to the field of optical coherence tomography (OCT), and in particular to spectral OCT wherein the depth position of object locations is determined from the wavelength spectrum of light scattered from the sample.

BACKGROUND OF THE INVENTION

OCT is a technique wherein imaging information can be obtained in the depth or z-direction of a sample, typically the retina of the eye. In conventional time domain OCT, the retina is scanned with a beam from an interferometer having a light source having a short coherence length, typically in the order of a few microns. A signal is obtained from the returned beam at depth positions wherein the optical path difference is less than the coherence length.

Different scanning techniques may be employed as described, for example, in U.S. Pat. No. 5,975,697, the contents of which are herein incorporated by reference. In the so-called A scan, the sample is scanned along a single axis in the depth direction to generate a reflectivity profile along the z axis at a particular point in the x-y plane. In a B scan, the sample is also scanned in either the x or y direction so as to generate a horizontal or vertical slice extending into the sample. The B-scan results from a succession of A scans. In en-face scanning, image slices in the x-y plane are taken at different depths.

In spectral OCT, described in U.S. Pat. No. 6,377,349 to Ferscher, the contents of which are herein incorporated by reference, and L. M. Smith and C. C. Dobson, Applied Optics, 1989, vol. 28, no. 15, pages 3339-3342, the spectrum of the light scattered by the object is obtained by a diode array in the object plane. In this case the optical A scan is obtained from a Fourier transform of the spectral intensity distribution of the light reflected by the object. Fourier transformation of the complex spectral amplitude gives information about the reflectivity of the sample along the z axis within the sample.

Spectral OCT is however subject to spectrometer losses and polarization effects, which can decrease the resolution obtainable. Instead of using a broadband source, it has been proposed to use a narrowband source, such as a laser, for the purpose of obtaining A scans. In this proposal, the frequency of the laser is modulated within a defined spectral band, and the response at each frequency within the spectral band recorded. Swept source scanning eliminates the need for a spectrometer since the different frequencies can be detected with a simple photodetector. Swept source scanning, however, has been limited to A scans, i.e. single axis scans extending in the depth direction, because it is difficult to obtain a stable frequency modulated source with a high sweep rate that would be required to perform a B scan (a sectional image extending in the depth direction). For example, assuming an image 1000 pixels wide and a frame rate of 1 frame/sec, the laser would need to sweep 1000 times/sec., which is very difficult to achieve in practice.

SUMMARY OF THE INVENTION

The present invention employs a frequency modulated laser wherein the image is scanned repeatedly at high speed along a scanning line in the x-y plane while the wavelength of the laser is modulated at a relatively low rate as the scanning beam moves across the image. Fourier transformation of the resulting data produces a B-scan image.

According to the present invention there is provided an apparatus for performing spectral OCT imaging on a target, comprising a scanner for repeatedly scanning said target along a transverse scanning line with an object beam derived from an OCT interferometer having a narrowband source; a modulator for modulating the wavelength of said narrowband source over a range of wavelengths at a rate that is slow relative to the rate of scanning said target; a detector for detecting the object beam returned from the target to produce a set of data obtained from multiple scans along said scanning line over said range of wavelengths; and a processor for processing said set of data to extract an OCT image of said target containing depth information.

The X-Y plane is normally considered the image or enface plane. The scanning in accordance with the principles of the invention takes place in this plane. Although reference is made to transverse scanning, it will be appreciated that the orientation in the X-Y plane is immaterial.

The processor typically produces a B-scan, although by scanning different lines in a raster fashion, it is of course possible to build up a set of data points containing complete three-dimensional image information for the target. These data points are stored in memory.

In effect, the method can be considered as building up the image one length at a time with each transverse scan corresponding to one wavelength, or actually a limited range of wavelengths depending on the sweep rate relative to the scan rate. In accordance with the inventive method the B-scan time is the same as the sweep rate of the source, allowing for much faster cross-sectional imaging than is possible in the prior art.

The scanning preferably takes place back and forth along the scanning line, with scans in both directions generating data.

According to another aspect of the invention there is provided an apparatus for performing spectral OCT imaging on a target, comprising a scanner for repeatedly scanning said target along a transverse scanning line with an object beam derived from an OCT interferometer having a narrowband source; a modulator for modulating the wavelength of said narrowband source over a range of wavelengths at a rate that is slow relative to the rate of scanning said target; a detector for detecting the object beam returned from the target to produce a set of data obtained from multiple scans along said scanning line over said range of wavelengths; and a processor for processing said set of data to extract an OCT image of said target containing depth information.

The scanner is preferably a galvo-scanner, for example a 16 KHz resonant scanner. A suitable scanning rate is 32,000 times per second.

BRIEF DESCRIPTION OF THE DRAWINGS

The invention will now be described in more detail, by way of example only, with reference to the accompanying drawings, in which:—

DETAILED DESCRIPTION OF THE PREFERRED EMBODIMENTS

Figure 1:
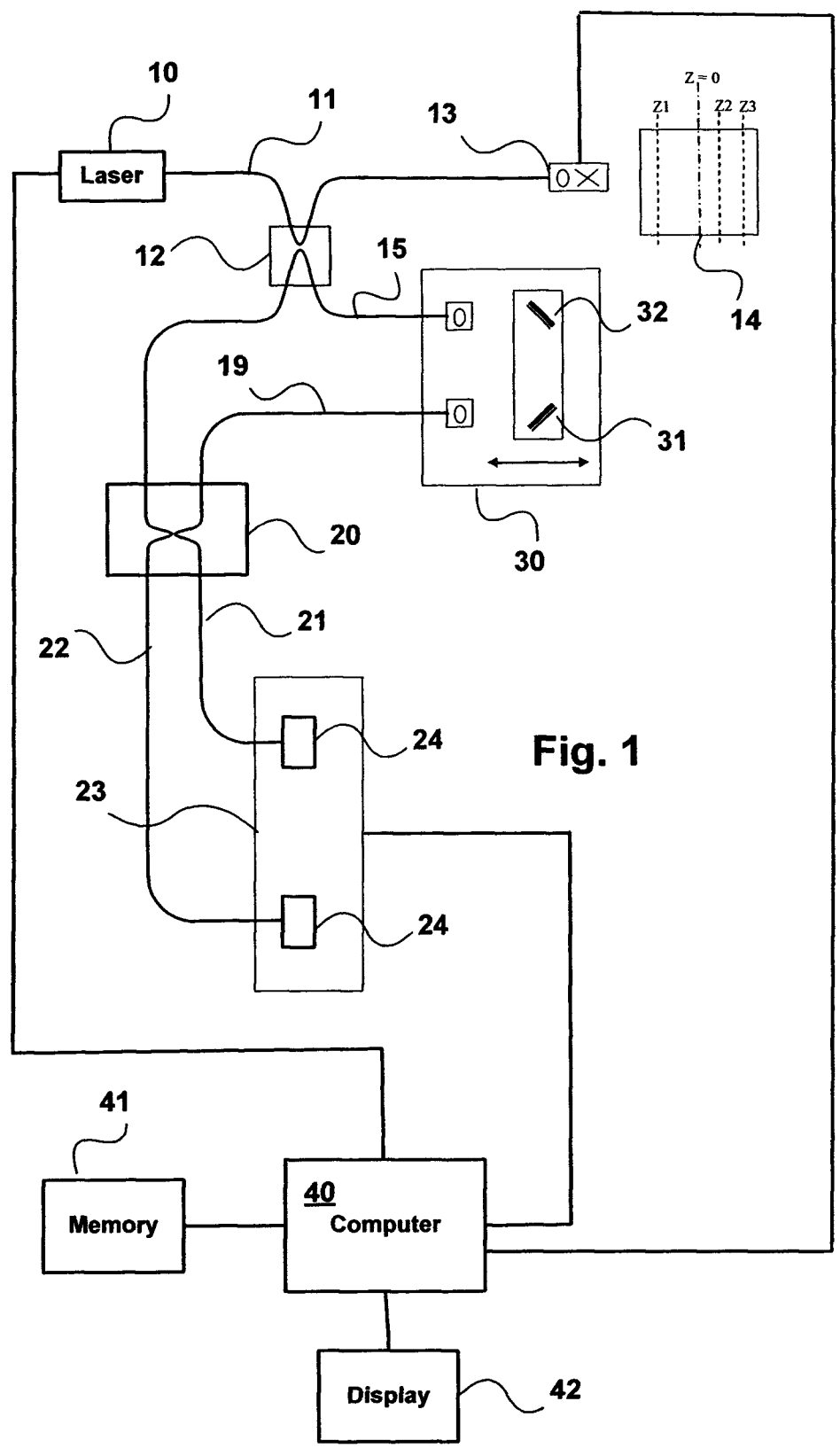
FIG. 1 is a schematic diagram of an OCT apparatus with a frequency modulated source.

FIG. 1 is a block diagram of a swept source OCT apparatus in accordance with the principles of the invention. While the invention is described in connection with fiber optics, it will be appreciated that it can also be implemented in bulk optics.

Figure 2:
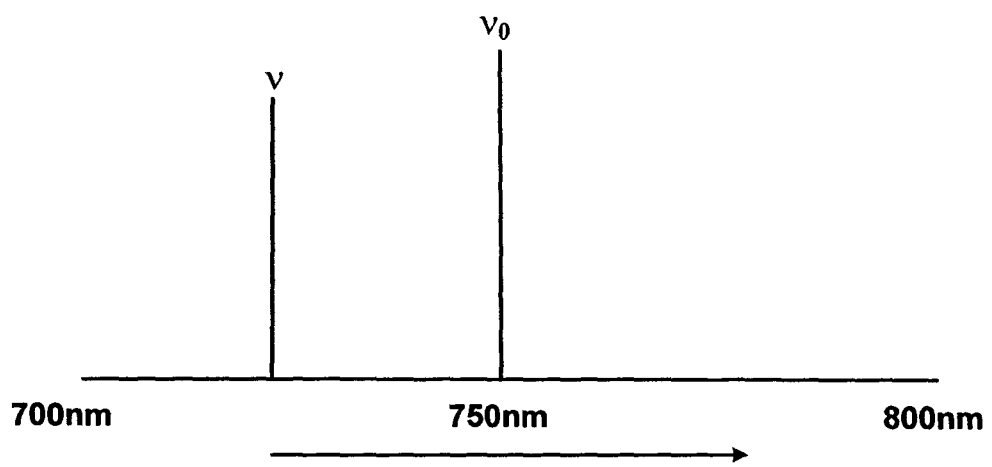
FIG. 2 is a spectral diagram of the light launched into the interferometer.

A laser 10, having a centre frequency of 750 nms produces an object light beam that is swept over a range 700-800 nms as shown in FIG. 2. The light output from the laser 10 is launched into optical fiber 11 forming part of an interferometer, from where it passes through splitter/combiner 12 to interface optics, which in the preferred embodiment comprises a galvo-scanner 13 for scanning the target 14. This is typically the retina of an eye, although the apparatus can be used for scanning any partially transparent target where depth information is required. The galvo-scanner 13 scans the target 14 in a raster fashion.

A portion of the input beam passes through the splitter/combiner 12 to optical fiber 15 to form the reference beam. Light from optical fiber 15 emerges into optical path length adjustment unit 30 including mirrors 31, 32, set at 45° angles and returns through optical fiber 19. Adjustment unit 30 allows the optical path difference between the object beam and reference beam to be adjusted, but unlike in the case of time-domain OCT, it is not necessary to vary the optical path difference to perform a depth scan in the target.

Light from the reference beam and the returned object beam is combined in splitter/combiner 20, where it interferes, and produces two differential output beams in optical fibers 21, 22, which are detected by photodetectors 24 in a balanced detection unit 23. In conventional spectral OCT, light is detected by a spectrometer. In the case of swept source OCT, it is sufficient merely to use a photodetector, since during a frequency sweep, different instants of time correspond to different frequencies. Of course, it is not necessary to use a balanced detection unit. The combined object and reference beams can be passed directly to a single photodetector.

Spectral OCT operates in the frequency domain. Due to the Fourier relationship between the auto correlation and the spectral power density, the depth scan can be calculated by a Fourier-transform from the acquired spectra. This feature improves imaging speed dramatically, while the reduced losses during a single scan improve the signal to noise proportional to the number of detection elements. The parallel detection at multiple wavelength ranges limits the scanning range, while the full spectral bandwidth sets the axial resolution.

The output of the detection unit 23 is passed to computer 40, which is connected to a display device 41 and a memory 21. The computer also acts as a modulator controlling the frequency/wavelength output by the laser 10 and the scanning of the galvo scanner 13.

In operation, the computer controls the galvo-scanner 13 to scan the target at a very high rate, typically many thousands of times per second. A 16 KHz resonant scanner, which can scan at the rate of 32,000 lines/sec, is suitable. The computer then controls the laser to sweep the frequency (or wavelength) at a low rate relative to the scanning rate of the galvo-scanner 13. In the case of a B-scan, or longitudinal sectional scan, the galvo-scanner scans back and forth at a high rate along a single scanning line. As it does so, the frequency of the source is swept at a rate that is slow relative to the rate of scanning of the target. Each scanning line is thus effectively performed at a particular frequency, or at least over a narrow range of frequencies determined by the change in frequency of the source during each transverse scan. performed at a particular frequency, or at least over a narrow range of frequencies determined by the change in frequency of the source during each transverse scan.

Each scanning line produces a subset of data points, each data point corresponding to an image point on the scanning line at a particular wavelength within the range of wavelengths. The number of the image points across the scanning line depends on the resolution of the system, which is determined by the clocking rate of the capture system in the computer. The captured data points are stored in memory 41.

Multiple scans then contain information obtained at different wavelengths as the wavelength of the source is swept slowly relative to the scan. By storing the data points from multiple scans the depth information can be extracted in a manner similar to conventional spectral OCT.

The computer 40 performs a Fast Fourier transform on the data and extracts image information extending in the depth direction by an amount that depends on the frequency range over which the source is swept. Multiple scans along a single scanning line permit information for constructing a longitudinal sectional image (B-scan) to be constructed. By scanning at different coordinates in the Y-direction, a complete three-dimensional image of the target can be constructed. The computer then displays the obtained data as a B-scan image on the display device 42.

Unlike the prior art, the swept source does not have a high sweep rate, so it can be made stable. Also, there is a considerable improvement in signal-to-noise ratio.

The invention claimed is:

1. A method of performing spectral optical coherence tomography imaging on a target, comprising:
   repeatedly scanning said target along a single transverse scanning line with an object beam derived from an optical coherence tomography interferometer having a tunable laser source so that the object beam moves back and forth along the single traverse scanning line;
   sweeping an output wavelength of said tunable laser source over a range of wavelengths while scanning said target such that the frequency of the turnable laser source is sweet at a rate that is slow relative to the rate of scanning said target so that each scanning line is performed at a particular wavelength within the range of wavelengths;
   detecting the object beam returned from the target to produce a set of data obtained from multiple scans along said single traverse scanning line over said range of wavelengths; and
   processing said set of data to extract an optical coherence tomography image of said target containing depth information.

2. A method as claimed in claim 1, wherein said target is scanned at least 10,000 times per second.

3. A method as claimed in claim 1, wherein said OCT image is a longitudinal sectional image (B-scan).

4. A method as claimed in claim 1, wherein said target is repeatedly scanned along different transverse scanning lines to obtain three-dimensional image information from the target.

5. A method as claimed in claim 1, wherein said processing involves performing a Fourier transform on said set of data points.

6. A method as claimed in claim 4, wherein said Fourier transform is a Fast Fourier transform.

7. A method as claimed in claim 1, wherein said target is scanned with a 16 KHz resonant scanner.

8. A method as claimed in claim 1, wherein said scanning is performed back and forth along a scanning line, with scans in each direction producing data.

9. An apparatus for performing spectral optical coherence tomography imaging on a target, comprising:
   a tunable laser for producing a reference beam and object beam in an optical coherence tomography interferometer;

a scanner for repeatedly scanning said target along a single transverse scanning line with the object beam so that the object beam moves back and forth along the single transverse scanning line;

a modulator for sweeping an output wavelength of said laser source over a range of wavelengths while said scanner scans said target such that the frequency of the source changes at a rate that is slow relative to the rate of scanning said target so that each scanning line is performed at a particular wavelength within the range of wavelengths;

a detector for detecting the object beam returned from the target to produce a set of data obtained from multiple scans along said scanning line over said range of wavelengths; and a processor for processing said set of data to extract an optical coherence tomography image of said target containing depth information.

10. An apparatus as claimed in claim 9, wherein said scanner is configured to scan the target at least 10,000 times per second.

11. An apparatus as claimed in claim 9, wherein processor produces a longitudinal sectional image (B-scan) of the target.

12. An apparatus as claimed in claim 9, wherein said scanner is controlled to repeatedly scan the target along different transverse scanning lines to obtain three-dimensional image information.

13. An apparatus as claimed in claim 9, wherein said processor is configured to perform a Fourier transform on said set of data points.

14. An apparatus as claimed in claim 13, wherein said Fourier transform is a Fast Fourier transform.

15. An apparatus as claimed in claim 9, wherein said scanner is a galvo scanner.

16. An apparatus as claimed in claim 15, wherein said scanner is a 16 Khz resonant scanner.

17. An apparatus as claimed in claim 15, wherein said scanner is configured to scan back and forth along the scanning line.

* * * * *